United States Patent
Hyde et al.

(10) Patent No.: US 9,709,987 B2
(45) Date of Patent: Jul. 18, 2017

(54) SYSTEMS AND METHODS FOR DEACTIVATING PLANT MATERIAL OUTSIDE OF A GROWING REGION

(71) Applicant: Elwha LLC, Bellevue, WA (US)

(72) Inventors: Roderick A. Hyde, Redmond, WA (US); Jordin T. Kare, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 380 days.

(21) Appl. No.: 14/448,746

(22) Filed: Jul. 31, 2014

(65) Prior Publication Data

US 2016/0029613 A1 Feb. 4, 2016

Related U.S. Application Data

(63) Continuation of application No. 14/448,750, filed on Jul. 31, 2014.

(51) Int. Cl.

| | |
|---|---|
| *G05D 1/00* | (2006.01) |
| *H01J 40/14* | (2006.01) |
| *F24J 2/00* | (2014.01) |
| *A01M 21/02* | (2006.01) |
| *G01N 33/00* | (2006.01) |
| *A01M 21/04* | (2006.01) |
| *G05B 15/02* | (2006.01) |
| *A01M 7/00* | (2006.01) |
| *A01G 1/00* | (2006.01) |
| *A01G 7/00* | (2006.01) |
| *G05D 1/02* | (2006.01) |
| *G06K 9/00* | (2006.01) |

(52) U.S. Cl.
CPC ........... *G05D 1/0094* (2013.01); *A01G 1/001* (2013.01); *A01G 7/00* (2013.01); *A01M 7/0042* (2013.01); *A01M 7/0089* (2013.01); *A01M 21/02* (2013.01); *A01M 21/04* (2013.01); *A01M 21/043* (2013.01); *G01N 33/0098* (2013.01); *G05B 15/02* (2013.01); *G05D 1/0219* (2013.01); *G06K 9/00791* (2013.01)

(58) Field of Classification Search
USPC .................... 701/28; 250/222.1; 126/569
See application file for complete search history.

(56) References Cited

U.S. PATENT DOCUMENTS

| | | | |
|---|---|---|---|
| 5,442,552 A | 8/1995 | Slaughter et al. | |
| 5,585,626 A * | 12/1996 | Beck ......................... | G01J 1/04 250/222.1 |
| 5,666,792 A | 9/1997 | Mullins | |
| 5,793,035 A * | 8/1998 | Beck ................... | A01M 7/0089 250/222.1 |
| 5,929,455 A | 7/1999 | Jensen | |
| 6,044,316 A | 3/2000 | Mullins | |
| 6,199,000 B1 | 3/2001 | Keller et al. | |

(Continued)

*Primary Examiner* — Thomas G Black
*Assistant Examiner* — Tyler Paige
(74) *Attorney, Agent, or Firm* — Foley & Lardner LLP

(57) ABSTRACT

A system for deactivating plant material outside of a growing region includes an emitter device configured to deactivate plant material, a sensor configured to remotely detect plant material outside of the growing region, and a controller configured to aim and activate the emitter device to deactivate the plant material in response to the plant material being detected by the sensor.

35 Claims, 9 Drawing Sheets

(56) References Cited

U.S. PATENT DOCUMENTS

| | | |
|---|---|---|
| 6,269,617 B1 | 8/2001 | Blanchard |
| 6,377,881 B1 | 4/2002 | Mullins |
| 6,553,299 B1 | 4/2003 | Keller et al. |
| 6,653,971 B1 | 11/2003 | Guice et al. |
| 6,853,328 B1 | 2/2005 | Guice et al. |
| 2001/0016053 A1* | 8/2001 | Dickson ............... G01J 3/2803 382/110 |
| 2002/0022928 A1 | 2/2002 | Ell |
| 2002/0022929 A1 | 2/2002 | Ell |
| 2002/0024665 A1* | 2/2002 | Masten ............... A01M 7/0089 356/328 |
| 2002/0035431 A1 | 3/2002 | Ell |
| 2002/0040300 A1 | 4/2002 | Ell |
| 2003/0036852 A1 | 2/2003 | Ell et al. |
| 2003/0187560 A1 | 10/2003 | Keller et al. |
| 2003/0208319 A1 | 11/2003 | Ell et al. |
| 2004/0034459 A1* | 2/2004 | Hoelscher ........... A01M 7/0089 701/50 |
| 2004/0136139 A1 | 7/2004 | Kummel |
| 2005/0184170 A1 | 8/2005 | Pannell et al. |
| 2008/0039974 A1 | 2/2008 | Sandin et al. |
| 2008/0109126 A1 | 5/2008 | Sandin et al. |
| 2008/0157990 A1 | 7/2008 | Belzer et al. |
| 2008/0196909 A1* | 8/2008 | Carlsson ............. A01D 34/835 172/720 |
| 2009/0099737 A1 | 4/2009 | Wendte et al. |
| 2009/0114210 A1* | 5/2009 | Guice ................... A01M 21/04 126/569 |
| 2009/0132132 A1 | 5/2009 | Peterson et al. |
| 2009/0192654 A1 | 7/2009 | Wendte et al. |
| 2009/0254218 A1 | 10/2009 | Sandin et al. |

* cited by examiner

SYSTEMS AND METHODS FOR DEACTIVATING PLANT MATERIAL OUTSIDE OF A GROWING REGION

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation of U.S. patent application Ser. No. 14/448,750, entitled SYSTEMS AND METHODS FOR DEACTIVATING PLANT MATERIAL OUTSIDE OF A GROWING REGION, naming Roderick A. Hyde, Jordin T. Kare, and Lowell L. Wood, Jr. as inventors, filed Jul. 31, 2014, which is currently co-pending or is an application of which a currently co-pending application is entitled to the benefit of the filing date.

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

RELATED APPLICATIONS

None

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

BACKGROUND

Plants of a particular type may grow within a field or other predetermined region. These plants may need to be prevented from spreading beyond the field or other predetermined region, or from intermixing with or contaminating plants outside of the field or predetermined region.

SUMMARY

One exemplary embodiment relates to a system for deactivating plant material outside of a growing region including an emitter device configured to deactivate plant material, a sensor configured to remotely detect plant material outside of the growing region, and a controller configured to aim and activate the emitter device to deactivate the plant material in response to the plant material being detected by the sensor.

Another exemplary embodiment relates to a method of deactivating plant material including establishing a boundary separating a growing region from an exclusion region, remotely detecting plant material in the exclusion region, targeting the detected plant material in the exclusion region, and emitting an emission at the targeted detected plant material to deactivate the targeted detected plant material.

Another exemplary embodiment relates to a system for deactivating plant material outside of a growing region including an emitter device configured to deactivate plant material, multiple sensors configured to remotely detect plant material outside of the growing region, and a controller configured to aim and activate the emitter device to deactivate the plant material in response to the plant material being detected by one or more of the sensors.

Another exemplary embodiment relates to a system for deactivating plant material outside of a growing region including a deactivation implement configured to physically deactivate plant material, a vehicle to which the deactivation implement is mounted, a sensor configured to remotely detect plant material outside of the growing region, and a controller configured to aim and activate the deactivation implement to physically deactivate the plant material in response to the plant material being detected by the sensor.

Another exemplary embodiment relates to a method of deactivating plant material including establishing a boundary separating a growing region from an exclusion region, remotely detecting plant material in the exclusion region, targeting the detected plant material in the exclusion region, and physically deactivating the targeted detected plant material.

Another exemplary embodiment relates to a system for deactivating plant material outside of a growing region including a sensor configured to remotely detect plant material outside of the growing region, an identifier device configured to identify the plant material by providing an identification in response to the plant material being detected by the sensor, a deactivator emitter configured to deactivate the plant material, and a controller configured to aim and activate the emitter device at the identification to deactivate the plant material.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
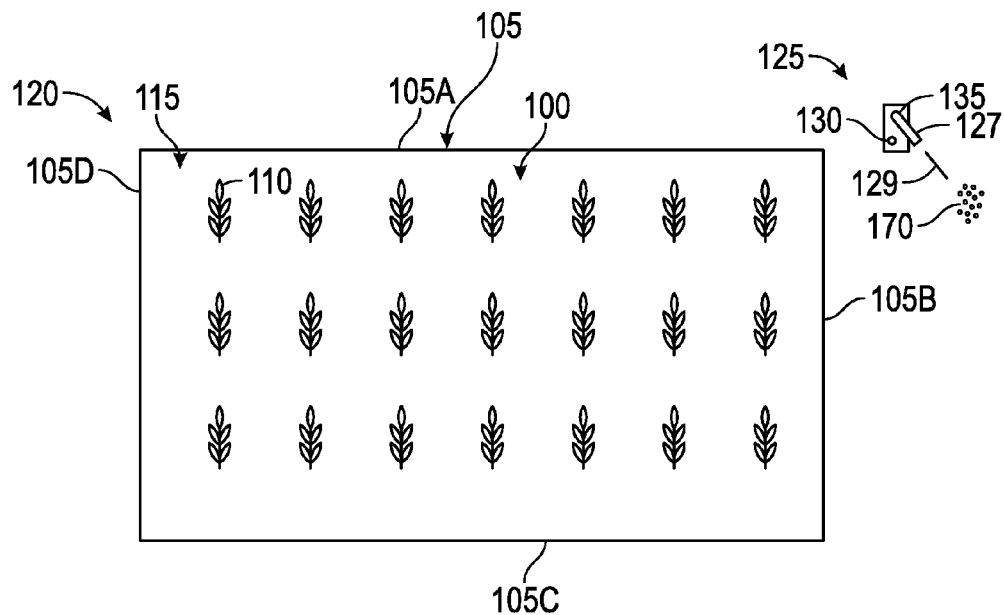
FIG. 1 is a schematic diagram of a system for deactivating plant material according to an exemplary embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In some circumstances, it is advantageous to contain plants within a specific field or other predetermined region. The plants to be contained may be undesirable outside of the predetermined region for one or more reasons including that the plants may undesirably crossbreed with other plants, may be poisonous or otherwise harmful to other plants and/or animals, may outgrow or otherwise force out other plants, or may be considered a nuisance. Further, such plants may need to be maintained as confidential (e.g., transgenic or other plants subject to research). In accordance with various embodiments described herein, such plants are contained by automatically detecting and deactivating and/or collecting plant material that has exited the predetermined region. In accordance with various embodiments described herein, such plants are contained by detecting plant material outside the predetermined region, in some embodiments analyzing the detected plant material, and deactivating and/or collecting plant material designated for exclusion from the predetermined region. In some embodiments, all plant material exiting the predetermined region is designated for deactivation. In other embodiments, a specific type or types of plants from the predetermined region are designated for deactivation when detected outside the predetermined region. "Deactivating" the plant material kills the plant material, prevents further growth of the plant material, eliminates the plant material's ability to reproduce, eliminates the plant material's ability to perform photosynthesis, or otherwise renders the plant material inert or unable to propagate (e.g., by destroying the plant's reproductive organs). "Collecting" the plant material physically gathers the plant material. Collecting is both a type of deactivating and an action that may be taken in addition to deactivating.

Referring to FIG. 1, field or predetermined region 100 is illustrated. Boundary 105 surrounds field 100 containing plants 110. Boundary 105 is illustrated as a four-sided polygon having sides 105A, 105B, 105C, and 105D surrounding field 100. However, a single side or edge (e.g., 105A, 105B, 105C, or 105D) can also be considered to be boundary. Boundary 105 defines growing region 115 and exclusion region 120, which are located on opposite sides of boundary 105.

Several exemplary embodiments of a system for deactivating plant material are illustrated in FIGS. 1-2, 4, 5-8, and 10-11. Each system includes one or more sensors that detects plant material that have exited or are exiting the growing region 115 to the exclusion region 120 and one or more emitter devices and/or deactivation implements configured to automatically deactivate and/or collect the plant material detected by the sensor. Plant material may be the plant itself, a reproductive component of the plant, a specific portion of the plant, etc. that is to be contained within growing region 115 and is unwanted in exclusion region 120 (i.e., outside of growing region 115). In some embodiments, the sensors monitor continuously and the emitter devices and/or deactivation implements react promptly to detected plant material so that plant material exiting growing region 115 is identified and deactivated and/or collected expeditiously. In some embodiments, the sensors may monitor for growing plant material periodically and the growing plant material may be deactivated and/or collected periodically.

Figure 2:
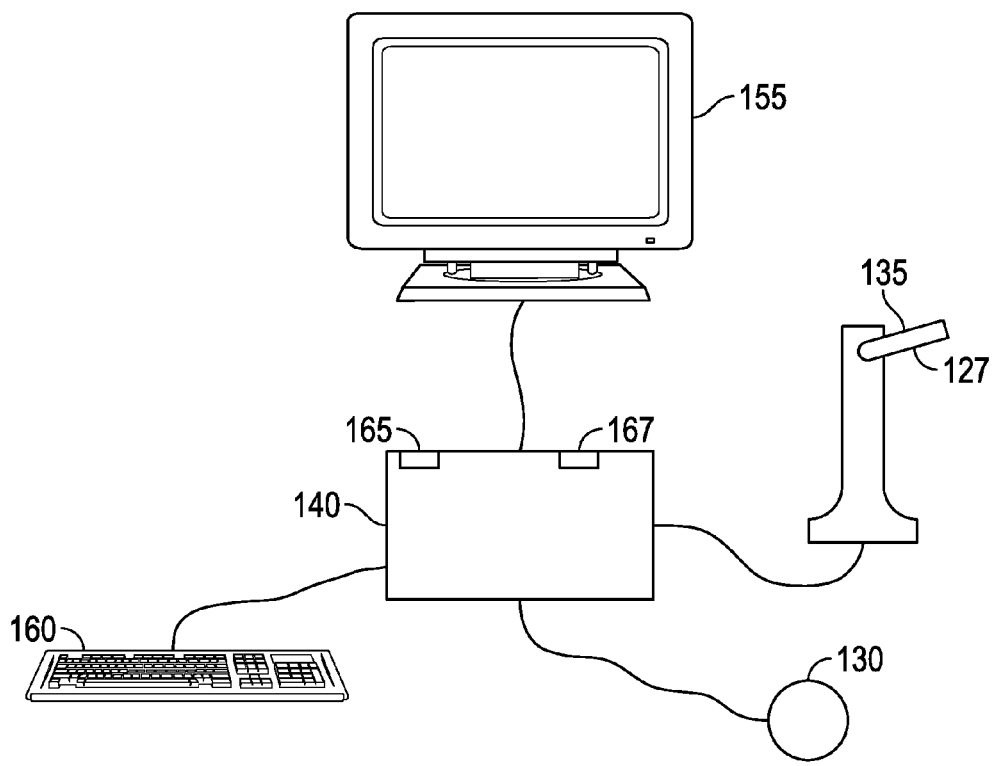
FIG. 2 is a schematic diagram of a system for deactivating plant material according to another exemplary embodiment.

Referring to FIGS. 1 and 2, exemplary embodiments of a system for deactivating plant material 125 are illustrated. System 125 includes sensor 130 and emitter device 135. In some embodiments, as shown in FIG. 1, sensor 130 and emitter device 135 are incorporated in a common stationary structure. In other embodiments, as shown in FIG. 2, sensor 130 and emitter device 135 are incorporated into separate stationary structures. System 125 also includes controller or processing circuit 140. Processing circuit 140 may be in communication with and control one or more emitters and one or more sensors. Processing circuit 140 includes processor 145 and memory 150.

Figure 3:
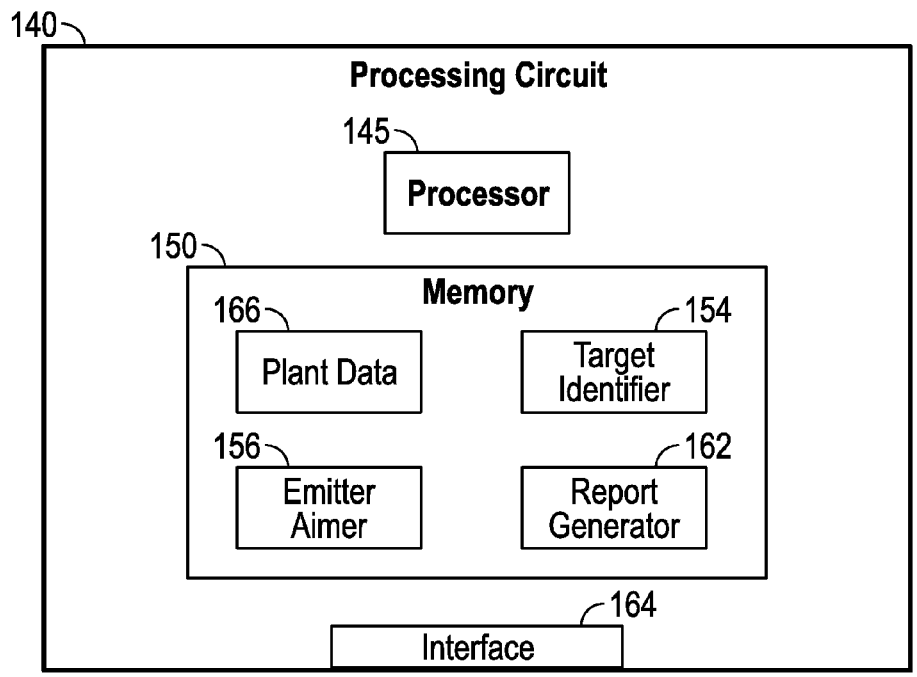
FIG. 3 is a block diagram of a processing circuit configured to control a system for deactivating plant material, according to an exemplary embodiment.

Referring to FIG. 3, a block diagram of processing circuit 140 is shown, according to an exemplary embodiment. Processor 145 may be or include one or more microprocessors (e.g., CPUs, GPUs, etc.), an application specific integrated circuit (ASIC), a circuit containing one or more processing components, a group of distributed processing components (e.g., processing components in communication via a data network or bus), circuitry for supporting a microprocessor, or other hardware configured for processing data. Processor 145 is also configured to execute computer code stored in memory 150 to complete and facilitate the activities described herein. Memory 150 can be any volatile or non-volatile computer-readable storage medium, or combinations of storage media, capable of storing data or computer code relating to the activities described herein. For example, memory 150 is shown to include computer code modules such as a target identifier module 154, an emitter aimer module 156, and a report generator module 162. When executed by processor 145, processing circuit 140 is configured to complete the activities described herein.

Processing circuit 140 also includes a hardware interface 164 for supporting the execution of the computer code target identifier module 154, emitter aimer module 156, and report generator module 162. Interface 164 may include hardware configured to receive data as input to processing circuit 140 (e.g. from input device 160) and/or communicate data as output to another computing device (e.g., to display 155). For example, processing circuit 140 may receive plant data 166 from one or more sensors (e.g., sensor 130), databases, or remote computing devices. Interface 164 may include circuitry to communicate data via any number of types of networks or other data communication channels. For example, interface 164 may include circuitry to receive and transmit data via a wireless network or via a wired network connection. In another example, interface 164 may include circuitry configured to receive or transmit data via a communications bus with other electronic devices.

Memory 150 may include plant data 166. In general, plant data 166 may include any data relating to the characteristics of one or more plants (e.g., plant type or species, the preferred method of deactivating the plant species, identifying characteristics of the plant species including spectroscopic properties, fluorescence properties, physical properties (e.g., size, shape, etc.), biological properties, genetic properties, the responsiveness of the plant species to non-visible light, genetic markers found in the plant species, etc.). In some embodiments, plant data 166 may include sensor data generated by one or more sensors 130 associated with system 125 (e.g. size, amount, etc. of the detected plant material). Sensor data may include, but is not limited to, data regarding the location of the detected plant material, data regarding the motion of the detected plant material (e.g., speed, velocity, direction of travel, etc.), data regarding environmental conditions detected by a sensor (e.g., wind speed, wind direction, weather type including rain, snow, fog, etc., water direction, water speed, etc.), and data regarding the boundary between the growing region and the exclusion region. Plant data 166 may also include user-provided data. User-provided data may include, but is not limited to, data regarding types of plant material, data regarding the plant material or materials to be deactivated, data regarding the boundary between the growing region and the exclusion region, data regarding the types of plant materials found within the growing region and within the exclusion region, and data regarding the components of the system to be controlled by the processing circuit.

Memory 150 may include target identifier module 154. Target identifier module 154 may be configured to determine the location of detected plant material relative to the emitter. In some embodiments, target identifier module 154 specifies detected plant material as targeted for deactivation by the emitter. In some embodiments, target identifier module 154 plots the boundary separating the growing region from the exclusion region (e.g., in response to a user input, in response to a sensor input, for example, from a GPS sensor, in response to the location of the emitter, in response to the location of the sensors, etc.)

Memory 150 may include emitter aimer module 156. Emitter aimer module 156 may be configured to aim the emitter at the targeted plant material and activate or fire the emitter at the targeted plant material. In some embodiments, emitter aimer module 156 causes a movable emitter to move to aim at the targeted plant material. In some embodiments, emitter aimer module 156 causes a vehicle to which the emitter is attached to move in order to aim at the targeted plant material. In some embodiments, emitter aimer module 156 selects one or more emitters from a group of stationary emitters for activation. In some embodiments, a separate emitter activation module is configured to activate or fire the emitter at the targeted plant material, not the emitter aimer module 156.

Memory 150 may include report generator module 162. Report generator module 162 may be configured to track and store data related to the sensors and/or emitters. In some embodiments, report generator module 162 stores data related to the number, amount, quantity, etc. of plant material detected by the sensor, the direction of plant material exiting the growing region 115, the portion of the boundary 105 where plant material is exiting the growing region 115, and generates a report containing this data or other information (e.g., information generated using this data as an input) that can be displayed to a user or otherwise output for other uses.

In some embodiments, system 125 includes a display 155 and an input device 160. Display 155 can include a display screen, multiple visual indicators (e.g., lights or LEDs), or other appropriate means for providing information to a user. Input device 160 can include a keyboard, a mouse, one or more buttons or switches, or other appropriate means for providing user inputs to the system. In some embodiments, display 155 and input device 160 are combined in a single device (e.g., a touch screen, a graphical user interface, etc.). In some embodiments, system 125 includes a communication device 165 configured to transfer data between the memory device 150 and a remote device (e.g., a separate computer, the internet, a central controller, etc.) and/or other components of the system (e.g., additional emitters or sensors). Communication device 165 can use Wi-Fi or other wireless communication methods, wired communication methods, or include a port for connecting a memory device (e.g., a USB drive or other disk drive). In some embodiments, boundary 105 is established by a user input to system 125 via input device 160. In some embodiments, mapping device 167 (e.g., a GPS device) is used to establish boundary 105. In some embodiments, boundary 105 is established based on detection range of sensor 130 or sensors included in the system (e.g., the limit of the sensor's range defines the boundary). Display 155 and input device 160 may be components of a handheld or portable device (e.g., a smart phone, tablet, laptop computer, etc.). A portable device allows the user to make changes or review the performance of the system from the field or remotely.

Sensor 130 remotely detects plant material (i.e., at a distance from sensor 130 itself). Plant material can include the plant itself, a reproductive component of the plant (e.g., seeds, pollen, spores, etc.) and can be naturally occurring plant material or transgenic or genetically modified plant material. In some embodiments, sensor 130 comprises an imaging sensor. The imaging sensor is capable of visually detecting and determining the motion of plant material (e.g., speed, direction, acceleration, etc.). The imaging sensor may be used in combination with a light source (e.g., to illuminate plant material or to excite a response (such as a fluorescent emission) from plant material that is responsive to UV-light or other light spectrums). In some embodiments, sensor 130 comprises a radar device. The radar device is capable of detecting and determining the motion of plant material via radio waves. In some embodiments, sensor 130 comprises a LIDAR device. The LIDAR device is capable of detecting and determining the motion of plant material via light waves. In some embodiments, sensor 130 comprises a spectroscope to analyze light (e.g., UV, IR, or other spectrums of light) reflected from or through plant material 170 to identify the presence of absence of one or more particular chemicals (either naturally occurring or genetically modified) in plant material 170 to identify the plant material.

In some embodiments, plant material 170 has been genetically-modified to be particularly susceptible to one or more specific methods of deactivation. For example, the plant material may be genetically modified to be particularly susceptible to a specific type of chemical and therefore easier to deactivate with a system using that chemical. As another example, the plant material may be genetically modified to be particularly susceptible to heat and therefore easier to deactivate with a laser or other heat delivery method of deactivation. Plant material 170 may also naturally respond to or be genetically-modified to respond to a particular stimulus. For example, the plant material may fluoresce in response to UV-light or other spectrums or may response physically (e.g., open or close leaves or flowers, etc.) in response to light (e.g., UV or other spectrums). Accordingly, sensor 130 may be paired with a light source or other stimulus source to provoke the response that sensor 130 is capable of detecting.

Emitter device 135 may target stationary plant material 170 detected by sensor 130 in exclusion region 120 (e.g., plant material 170 on the ground). Emitter device may target moving plant material 170 detected by sensor 130 in exclusion region 120 (e.g., airborne or waterborne plant material 170).

Emitter device 135 comprises a movable emitter 127 that emits a beam, a spray, a cloud, or other substance to deactivate plant material. Movable emitter 127 is movable (e.g., rotatable, translatable) to create one or more degrees of freedom to allow movable emitter 127 to be aimed at or target plant material 170 detected by sensor 130. After targeting the plant material 170, movable emitter 127 emits a beam (e.g., laser, microwave, ultraviolet light, x-ray, particle beam, a beam of chemicals, etc.) a spray (e.g., a chemical spray, etc.), a cloud (e.g., a cloud or fog of aerosol chemicals, etc.), a projectile (e.g., a breakable capsule or bullet containing a chemical), a high temperature stream (e.g., hot air as a stream or jet, steam as a stream or jet, fire as a stream or jet, a flamethrower, etc.) or another substance to deactivate the targeted plant material 170 (collectively, an "emission"). As shown in FIG. 1, in some embodiments, movable emitter 127 comprises a movable beamed energy emitter (e.g., a laser emitter, a microwave emitter) that emits beam 129 to deactivate plant material 170 (shown in FIG. 1 as stationary reproductive components located in exclusion region 120) by heating the plant material. In other embodiments, movable emitter 127 comprises a movable chemical emitter (e.g., for emitting a chemical spray or for emitting an aerosol chemical) for deactivating the plant material with chemicals (e.g., pesticides, herbicides, other appropriate biological agents, etc.). In other embodiments, movable emitter 127 comprises a movable high temperature emitter (e.g., a movable torch for emitting a hot air stream or jet, a steam stream or jet, a stream or jet of fire) for deactivating the plant material by heating the plant material. In some embodiments, system 125 includes multiple emitter devices 135, each employing a different one of the methods for deactivating plant material described above. In this way, a combination of methods for deactivation can be used when attempting to deactivate plant material. In other embodiments, system 125 includes multiple emitter devices 135, each employing the same method for deactivating plant material. In this way, the multiple emitter devices 135 provide redundancy in case of failure or malfunction of one of the emitter devices 135.

Figure 4:
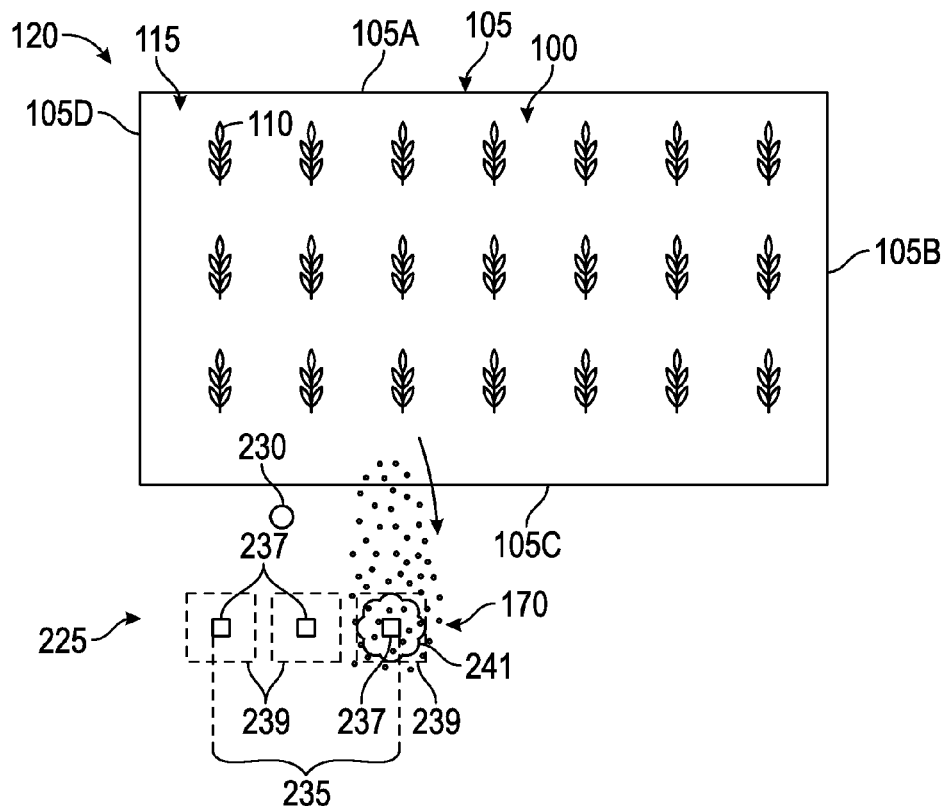
FIG. 4 is a schematic diagram of a system for deactivating plant material according to another exemplary embodiment.

Referring to FIG. 4, system 225 is an exemplary embodiment of another stationary system for deactivating plant material. System 225 is similar to system 125 and may include, in various embodiments, components similar to those described above with respect to system 125.

System 225 includes sensor 230 and emitter device 235, which are incorporated in separate structures. Emitter device 235 includes multiple fixed emitters 237, each of which defines a deactivation zone 239 in which the corresponding emitter may emit a beam, a spray, a cloud, or another emission as described above to deactivate plant material. Processing circuit determines the deactivation zone 239 in which the detected plant material 170 is located and aims at or targets the detected plant material 170 by selecting the corresponding fixed emitter 237 for activation to deactivate the detected plant material 170. In some embodiments, deactivation zones 239 of adjacent fixed emitters 237 overlap. Activating the fixed emitter 237 causes it to emit an emission as described above. In some embodiments, fixed emitter 237 comprises a fixed beamed energy emitter (e.g., a laser emitter, a microwave emitter). As shown in FIG. 4, in other embodiments, fixed emitter 237 comprises a fixed chemical emitter that emits a cloud of aerosol chemicals 241 (e.g. a herbicide) to deactivate plant material 170 (shown in FIG. 4 as windborne reproductive components traveling in exclusion region 120 in the direction shown by the arrow). In other embodiments, a fixed chemical emitter emits a chemical spray. In some embodiments, the duration and amount of chemical emission is varied based on input from sensor 230 (e.g., in response to amount of plant material detected) or other sensors (e.g., a wind speed and direction sensor so that the chemical emission is not blown away before reaching the targeted detected plant material).

Figure 5:
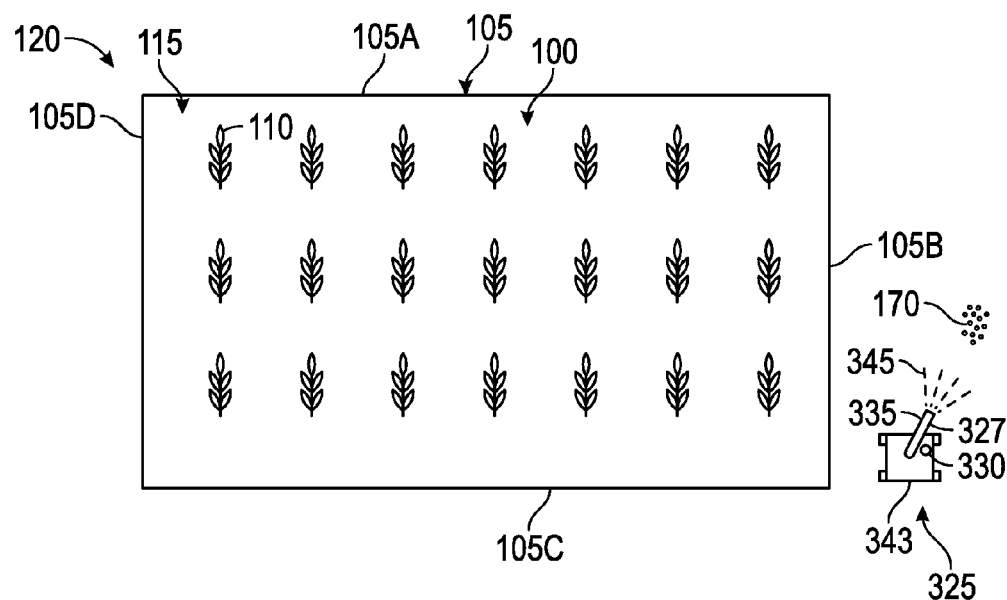
FIG. 5 is a schematic diagram of a system for deactivating plant material according to another exemplary embodiment.

Referring to FIG. 5, system 325 is an exemplary embodiment of a mobile system for deactivating plant material. System 325 is similar to system 125 and may include, in various embodiments, components similar to those described above with respect to system 125.

System 325 includes sensor 330, emitter device 335, and ground vehicle 343. In some embodiments, as shown in FIG. 5, sensor 330 and emitter device 335 are mounted to ground vehicle 343. In other embodiments, only one of sensor 330 and emitter device 335 is mounted to ground vehicle 343 with the other incorporated in a separate structure (e.g., a stationary mounting structure, a second vehicle, etc.). Ground vehicle 343 is capable of moving over the ground. Ground vehicle 343 may include one or more wheels, tracks, legs, or other devices (e.g., hover devices) suitable for movement on or over ground. Ground vehicle 343 may be configured to patrol boundary 105. The patrol can be uniformly distributed along boundary 105 or concentrated along a particular targeted portion of boundary 105 (e.g., boundary side 105B). A vehicle may continuously or periodically patrol the boundary, or may be directed to specific portions of the boundary or exclusion area by a controller upon detection of plant material by a sensor. Also, the same vehicle may be dispatched on patrols of multiple boundaries (e.g., for a large field having multiple exclusion areas). In some embodiments, as shown in FIG. 5, emitter device 335 comprises movable emitter 327. In other embodiments, emitter device 335 is a fixed emitter. As shown in FIG. 5, movable emitter 327 is a chemical emitter emitting chemical spray 345 to deactivate the targeted plant material (shown as stationary reproductive components located in exclusion region 120).

Figure 6:
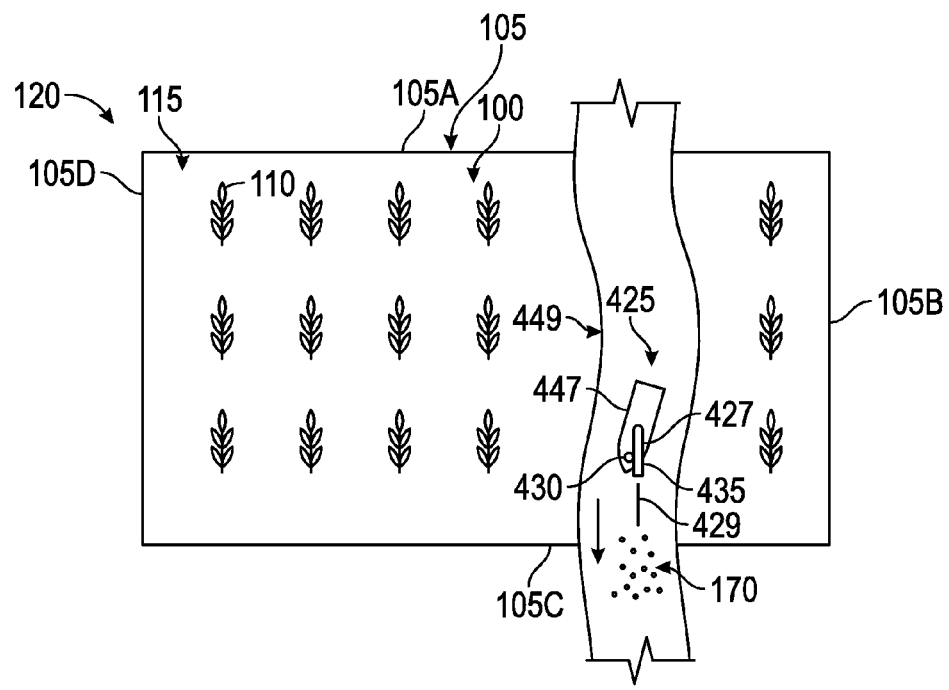
FIG. 6 is a schematic diagram of a system for deactivating plant material according to another exemplary embodiment.

Referring to FIG. 6, system 425 is another exemplary embodiment of another mobile system for deactivating plant material. System 425 is similar to systems 125 and 325 and may include, in various embodiments, components similar to those described above with respect to systems 125 and 325.

System 425 includes sensor 430, emitter device 435, and water vehicle 447. Water vehicle 447 (e.g., a boat, a hovercraft, etc.) is capable of moving through or over water (e.g., stream 449). As shown in FIG. 6, movable emitter 427 is a beamed energy emitter emitting beam 429 to deactivate the targeted plant material 170 (shown as waterborne reproductive plant material traveling in exclusion region 120 in the direction shown by the arrow).

Figure 7:
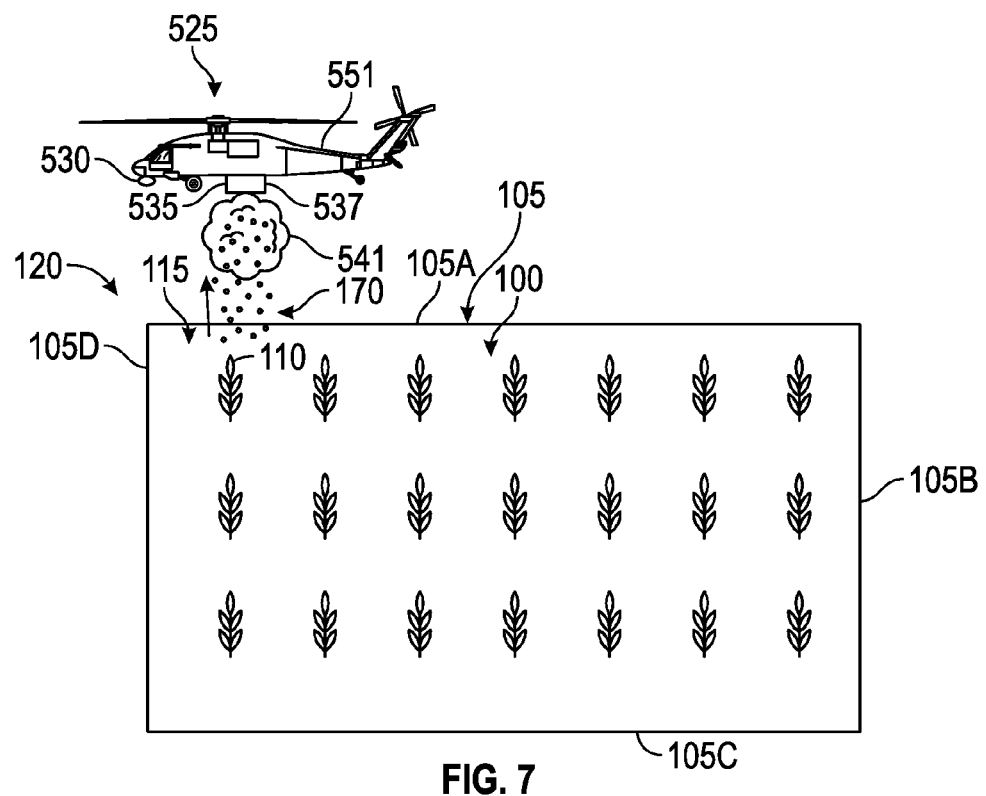
FIG. 7 is a schematic diagram of a system for deactivating plant material according to another exemplary embodiment.

Referring to FIG. 7, system 525 is another exemplary embodiment of another mobile system for deactivating plant material. System 525 is similar to systems 125, 325, and 425 and may include, in various embodiments, components similar to those described above with respect to systems 125, 325, and 425.

System 525 includes sensor 530, emitter device 535, and air vehicle 551. Air vehicle 551 (e.g., a helicopter, a plane, an unmanned aerial vehicle ("UAV"), a balloon, etc.) is capable of moving through the air. UAVs may include vertical-takeoff and landing aircraft, fixed wing aircraft, helicopters, etc. Different types of UAV maybe piloted autonomously by an onboard controller or computer or may be piloted by the remote control of a pilot on the ground or in another vehicle. A UAV may be a component of a unmanned aircraft system ("UAS") that also includes control system (e.g., a ground control station), a control link between the UAV and the ground control station (e.g., a radio control link, a specialized datalink, etc.), and may include other related support equipment (e.g., equipment for servicing the UA, equipment associated with takeoff and landing of the UAV, etc.). As shown in FIG. 7, fixed emitter 537 is a chemical emitter emitting a cloud of aerosol chemicals 541 to deactivate the targeted plant material 170 (shown as airborne reproductive components traveling in exclusion region 120 in the direction shown by the arrow).

Figure 8:
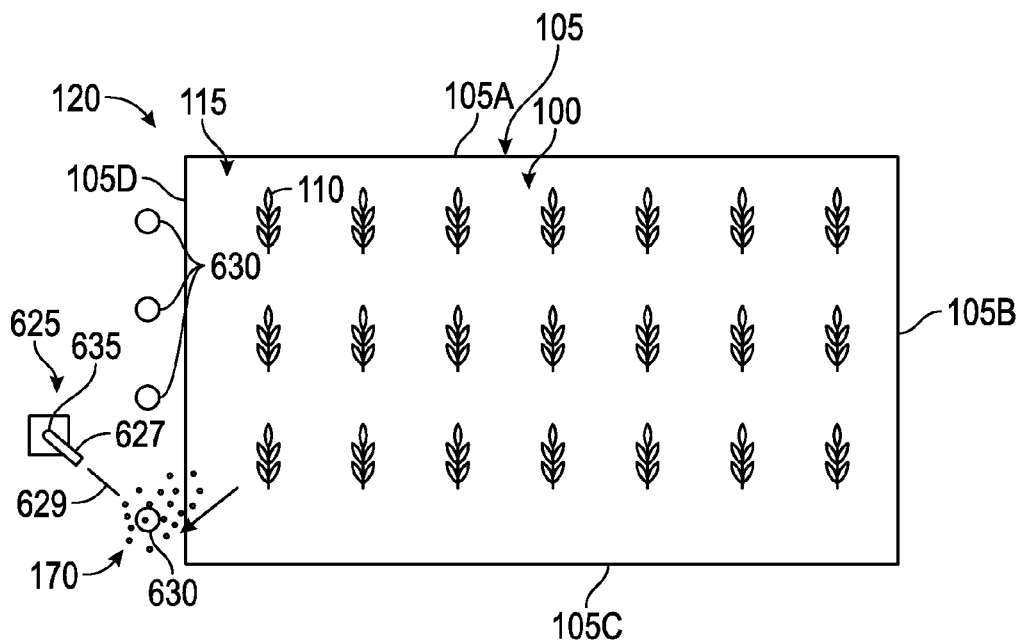
FIG. 8 is a schematic diagram of a system for deactivating plant material according to another exemplary embodiment.

Referring to FIG. 8, system 625 is an exemplary embodiment of another stationary system for deactivating plant material. System 625 is similar to systems 125 and 225 and may include, in various embodiments, components similar to those described above with respect to systems 125 and 225.

System 625 includes multiple sensors 630 and emitter device 635, which are incorporated in separate structures. Emitter device 635 is configured to automatically deactivate plant material 170 detected by one or more of sensors 630. As shown in FIG. 8, emitter device 635 comprises movable beamed energy emitter 627 that emits beam 629 to deactivate plant material 170 (shown as airborne reproductive components traveling in exclusion region 120 in the direction shown by the arrow). Multiple sensors 630 may be arranged as a sensor fence or picket line along a portion of the boundary 105. In some embodiments, such a sensor fence may be used to define the boundary 105. In some embodiments, sensors of two or more types may be employed (e.g., optical and radar sensors). In some embodiments, sensors may be employed in two or more configurations (e.g., fixed sensors which provide initial detection and approximate location of plant material, and sensors mounted on ground or air vehicles which provide additional location sensing for aiming and activating vehicle-mounted emitters). Multiple sensors 630 can be combined in different manners. For example, multiple sensors of the same type could be used for redundancy. Multiple sensors of different types could be used to detect different types of plant materials or to use multiple methodologies to detect the same type of plant material. Multiple sensors can also be used to perform complimentary tasks. For example, relatively long range radar could detect plant material leaving the boundary and then a vehicle with a relatively shorter range sensor for determining the type of plant material could be dispatched to identify the plant material based on the location of the plant material detected by the radar. In some embodiments, sensors may be employed in two or more configurations, e.g., a fixed sensor which provides initial detection and approximate location of the plant material, and sensors mounted on a vehicle which provides additional location sensing for aiming and activating a vehicle-mounted or fixed location emitter.

Figure 9:
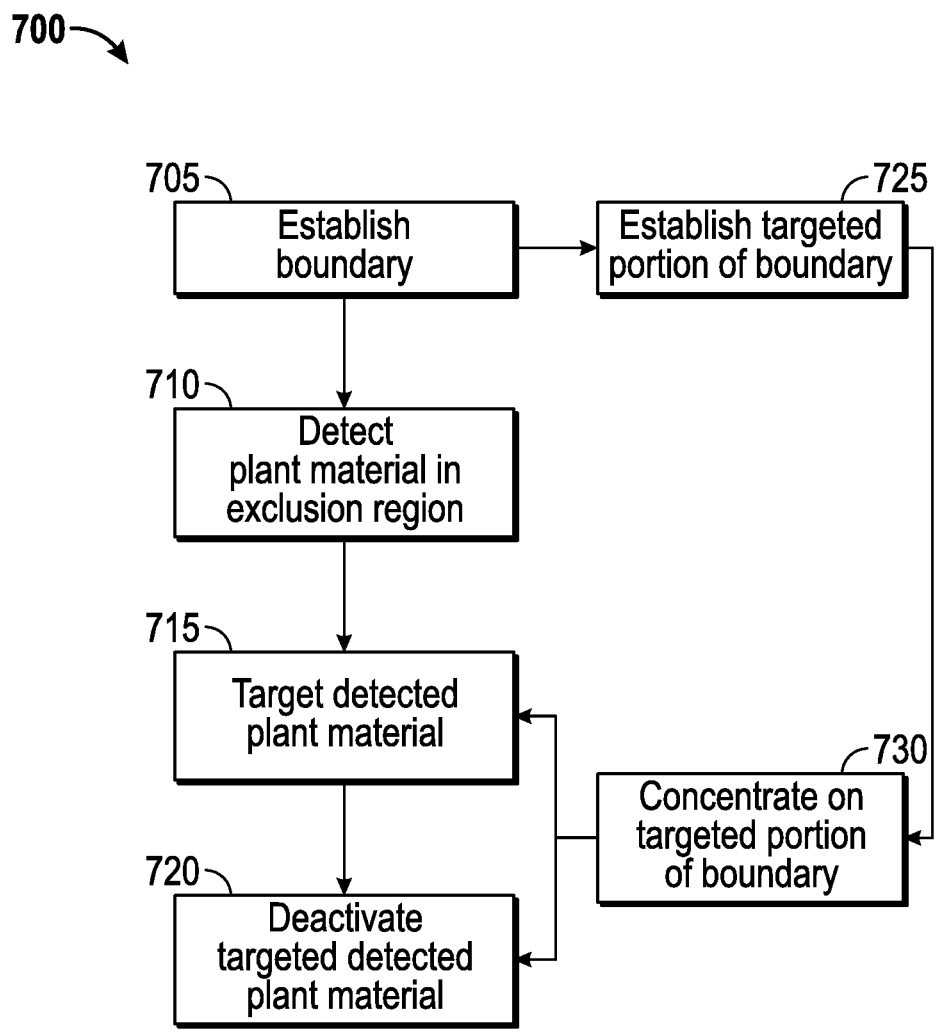
FIG. 9 is a flow chart of a method of deactivating plant material according to an exemplary embodiment.

Referring to FIG. 9, a method of deactivating plant material 700 is illustrated according to an exemplary embodiment. In some embodiments, method 700 is implemented by one or more of systems 125, 225, 325, 425, 525, 625, 825, and 925. A boundary (e.g., boundary 105) is established separating a growing region (e.g., growing region 115) from an exclusion region (e.g., exclusion region 120) (step 705). Plant material (e.g. plant material 170) is detected (e.g., by sensor 130) in the exclusion region (step 710). The detected plant material is targeted (e.g., by emitter device 135) (step 715). An emission as described above, is emitted at the targeted detected plant material to deactivate the targeted detected plant material (step 720). Alternatively, a deactivation implement (e.g., deactivation implement 831 described below) is used in place of or in addition to the emission to deactivate the targeted detected plant material.

In some embodiments, method 700 also includes establishing a targeted portion (e.g. side 105B) of the boundary (e.g., boundary 105) (step 725). In some embodiments, the targeted portion of the boundary is identified in response to known circumstances likely to result in plant material exiting the growing region to the exclusion region at the targeted portion of the boundary. For example, wind direction may dictate the direction and location from which airborne plant material can be expected to exit the growing region. As another example, moving sources of water (e.g., stream 449) are known to flow in a specific direction, which will dictate the direction and location from which waterborne plant material can be expected to exit the growing region. As another example, the reproductive cycle of the plants (e.g., plants 110) within different portions of the growing region is known and the portions of the boundary close to the portions of the growing region expected to produce reproductive components (e.g., seeds, pollen, spores) would be the targeted portion of the boundary. Targeting (steps 715) and emitting (step 720) is concentrated on the targeted portion of the boundary (e.g., by increasing vehicle patrol time along the targeted portion of the boundary, by increasing number of sensors and/or emitter devices along the targeted portion of the boundary, etc.) (step 730). In this way, more plant material deactivating resources are brought to bear along the targeted portion of the boundary.

Figure 10:
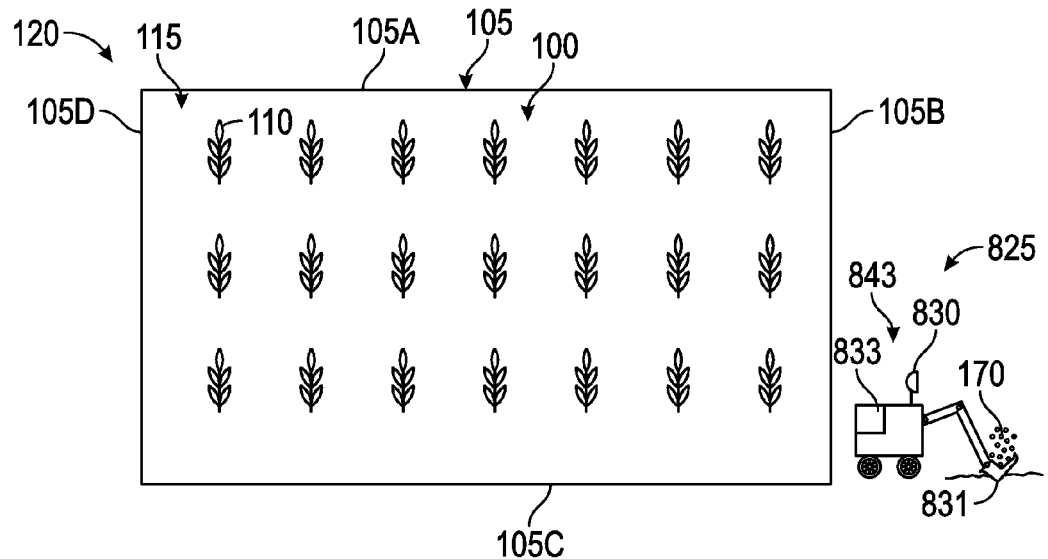
FIG. 10 is a schematic diagram of a system for deactivating plant material according to another exemplary embodiment.

Referring to FIG. 10, system 825 is another exemplary embodiment of another mobile system for deactivating plant material. System 825 is similar to systems 125, 325, 425, and 525 and may include, in various embodiments, components similar to those described above with respect to systems 125, 325, 425, and 525.

System 825 includes sensor 830, deactivation implement 831 and ground vehicle 843. Deactivation implement 831 is configured to physically deactivate plant material by physically destroying plant material and/or physically capturing and removing plant material from the exclusion region 120. For example, the deactivation implement 831 may be one or more shovels, spades, hoes, picks, blades, nets, sieves, manipulator arms, vacuums, or other device suitable to destroy and/or collect plant material. As shown in FIG. 10, deactivation implement 831 is a shovel. In embodiments where deactivation implement 831 physically collects and removes plant material (e.g., with a shovel, spade, net, sieve, manipulator arm, or vacuum), ground vehicle 843 may include a collection chamber 833 for storing plant material collected by deactivation implement 831. As shown in FIG. 10, sensor 830 and deactivation implement 831 are mounted to ground vehicle 843. In other embodiments, one or more sensors 830 are mounted remotely from ground vehicle 843 in a separate structure (e.g., a stationary mounting structure, a second vehicle, etc.). In some embodiments, ground vehicle 843 is replaced by a water vehicle or an air vehicle. In some embodiments, deactivation implement 831 is included in place of an emitter device (e.g., emitter device 135). In other embodiments, deactivation implement 831 is included in addition to one or more emitter devices. In this way, the emitter device may be used to deactivate plant material and the deactivation implement 831 may be used to destroy and/or collect the deactivated plant material. Capturing the plant material may be valuable when the plant material needs to be maintained as confidential, by not only deactivating the plant material in the exclusion region 120, but then also collecting the deactivated plant material, thereby maintaining the confidentiality of even the deactivated plant material. In some embodiments, system 825 includes more than one deactivation implements.

Figure 11:
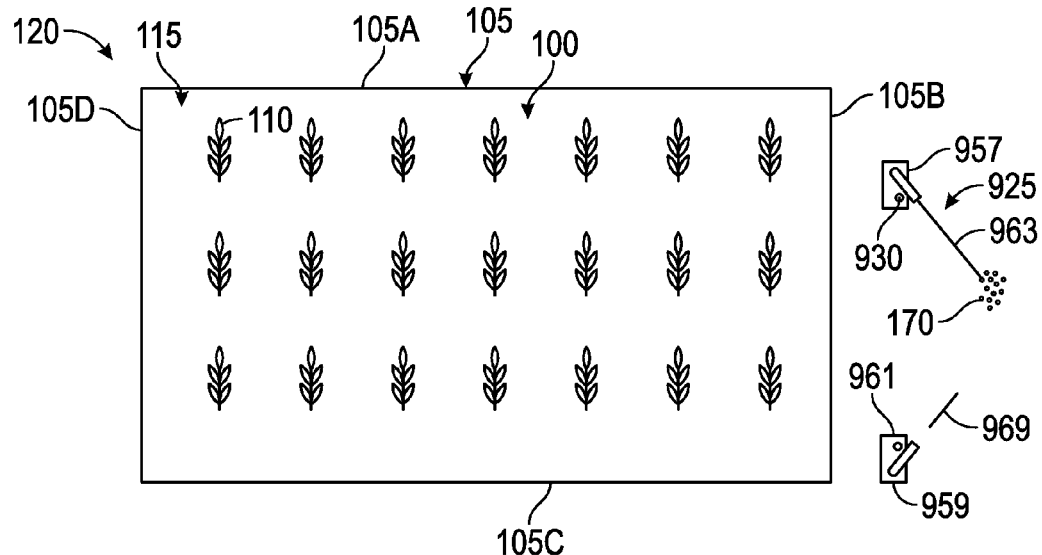
FIG. 11 is a schematic diagram of a system for deactivating plant material according to another exemplary embodiment.

Referring to FIG. 11, system 925 is an exemplary embodiment of another stationary system for deactivating plant material. System 925 is similar to systems 125, 225, and 625 and may include, in various embodiments, components similar to those described above with respect to systems 125, 225, and 625.

System 925 includes one or more sensors 930 configured to detect plant material, and two or more emitter devices, one of which functions as a identifier device 957 and the other of which functions as a deactivator emitter 959, and identification sensor 961. The identifier device 957 identifies or marks the plant material detected by sensor 930 by providing an identification. This identification may take the form of a targeting beam emitted by a beamed energy emitter (e.g., a laser emitter emitting a targeting laser beam) that can be detected by identification sensor 961 (e.g., a laser detector or laser seeker), a physical marking such as a paint or dye emitted by a physical marking emitter that can be detected by identification sensor 961 (e.g., visible to an imaging sensor or detectable by another appropriate type of sensor to identify the physically marked plant material), or the storing of location information (e.g., on a coordinate system describing the exclusion region 120, as a GPS coordinate, etc.) in memory (e.g., in memory 150 as plant data 166) that can be identified by retrieving the location information from memory. The physical marking may respond to electromagnetic radiation (visible light, nonvisible light like ultraviolet or infrared, etc.), with a response for example, through fluorescence or phosphorescence. This response may be detected by identification sensor 961 (e.g., an imaging sensor, a light sensor, or other appropriate type of sensor to identify the response).

The deactivator emitter 959 is targeted or aimed at the identified plant material as detected by identification sensor 961 and activated to emit an emission as described above to deactivate the targeted plant material.

In some embodiments, as shown in FIG. 11, identifier device 957 is a beamed energy emitter as described above that emits a targeting beam 963, and deactivator emitter 959 is also a beamed energy emitter that emits a deactivating beam 969 having a higher power output than targeting beam 963. In use, sensor 930 detects plant material 170 in exclusion region 120. The identifier device 957 targets the detected plant material 170 and emits targeting beam 963. Identification sensor 961 detects targeting beam 963 hitting the targeted plant material 170. Deactivator emitter 959 is targeted at the identified plant material in response to signals from identification sensor 961 and emits deactivating beam 969 to deactivate the identified plant material.

Alternatively, system 925 may be implemented as a mobile system similar to mobile systems 325, 425, 525, and 825 described above. In such mobile systems, the identifier device 957 may be mounted to the vehicle or mounted remotely from the vehicle in a separate structure (e.g., a stationary mounting structure, a second vehicle, etc.).

Figure 12:
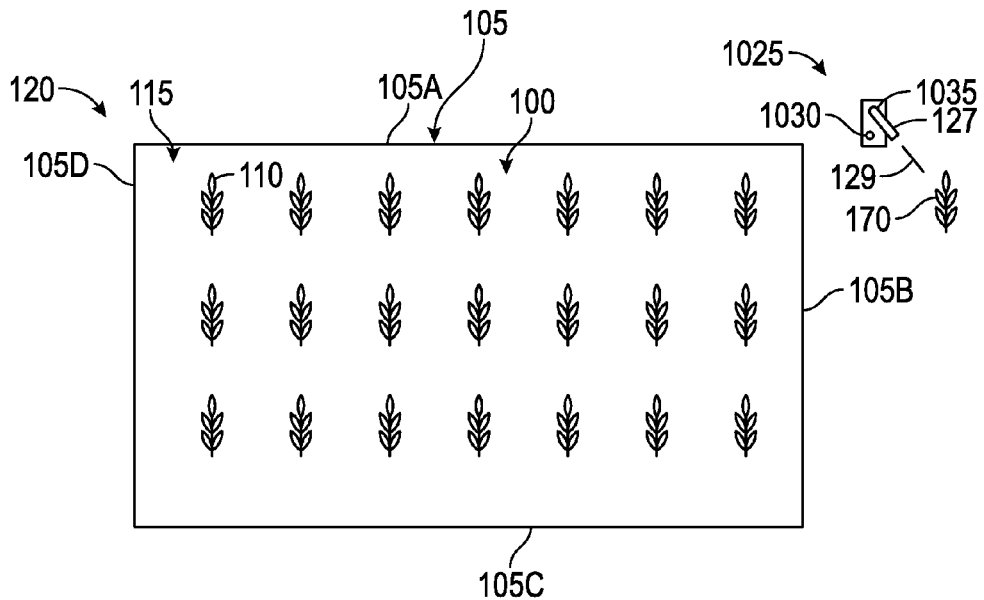
FIG. 12 is a schematic diagram of a system for deactivating plant material according to another exemplary embodiment.
Figure 14:
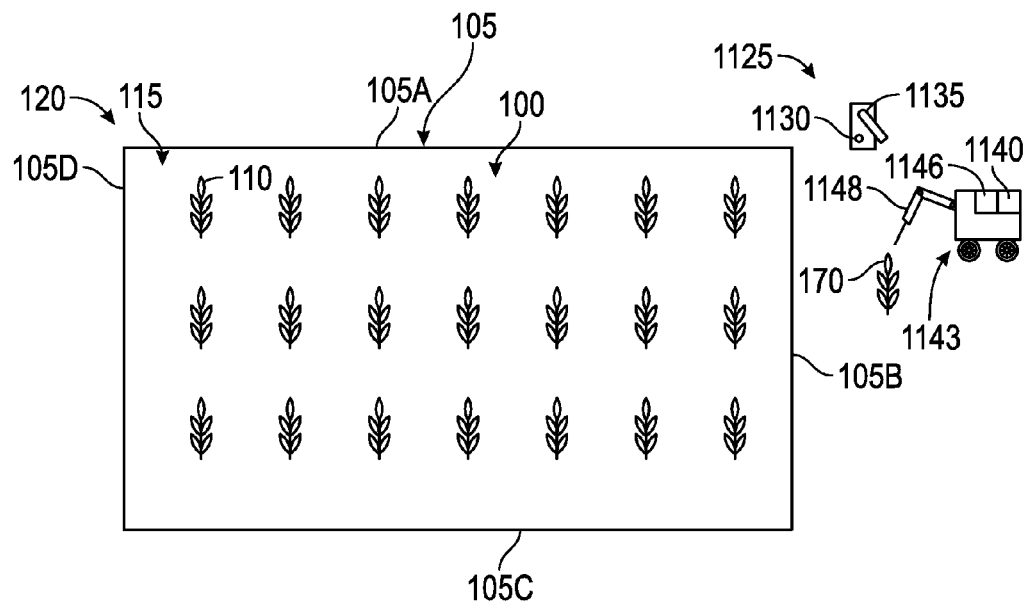
FIG. 14 is a schematic diagram of a system for deactivating plant material according to another exemplary embodiment.

Exemplary embodiments of a system for deactivating plant material are illustrated in FIGS. 12 and 14. Growing plant material may be plants, sprouts, seeds, runners, portions of a plant, etc. that have begun to grow in the exclusion region 120 (i.e., outside of growing region 115). In some embodiments, all growing plant material is designated for exclusion from the exclusion region 120. In other embodiments, specific growing plant material is designated for exclusion from the exclusion region 120 (e.g., transgenic plant material that is desired to be contained exclusively within the growing region 115). In some embodiments, the sensors may monitor for growing plant material periodically and the growing plant material may be deactivated and/or collected periodically. The timing of these monitoring and deactivating/collecting operations may vary depending on the types of sensors used to detect the plant material and on the type of equipment used to carry out the deactivation and/or collection operation. For example, monitoring could be carried out hourly, daily, weekly, or monthly and deactivating/collecting could be carried out on the same or different time scales.

Referring to FIG. 12, an exemplary embodiment of a system for deactivating plant material 1025 is illustrated.

System 1025 includes sensor 1030 and emitter device 1035. In some embodiments, as shown in FIG. 12, sensor 1030 and emitter device 1035 are incorporated in a common stationary structure. In other embodiments, sensor 1030 and emitter 1035 are incorporated into separate stationary structures. System 1025 also includes controller or processing circuit 1040. Processing circuit 1040 may be in communication with and control one or more emitters and one or more sensors. Processing circuit 1040 includes processor 1045 and memory 1050.

Figure 13:
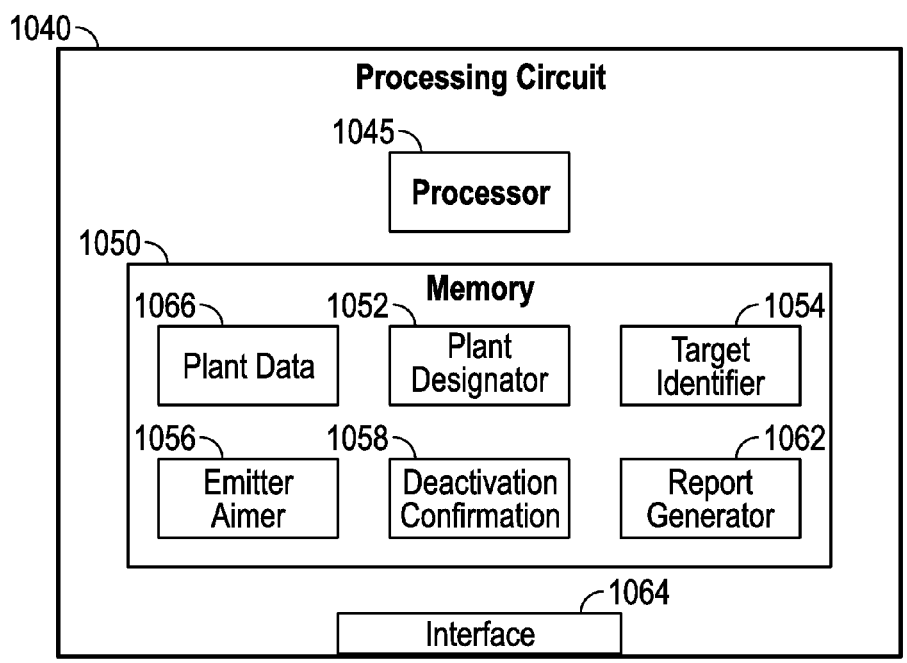
FIG. 13 is a block diagram of a processing circuit configured to control a system for deactivating plant material, according to an exemplary embodiment.

Referring to FIG. 13, a block diagram of processing circuit 1040 is shown, according to an exemplary embodiment. Processor 1045 may be or include one or more microprocessors (e.g., CPUs, GPUs, etc.), an application specific integrated circuit (ASIC), a circuit containing one or more processing components, a group of distributed processing components (e.g., processing components in communication via a data network or bus), circuitry for supporting a microprocessor, or other hardware configured for processing data. Processor 1045 is also configured to execute computer code stored in memory 1050 to complete and facilitate the activities described herein. Memory 1050 can be any volatile or non-volatile computer-readable storage medium, or combinations of storage media, capable of storing data or computer code relating to the activities described herein. For example, memory 1050 is shown to include computer code modules such as a plant designator module 1052, a target identifier module 1054, an emitter aimer module 1056, a deactivation confirmation module 1058, and a report generator module 1062. When executed by processor 1045, processing circuit 1040 is configured to complete the activities described herein.

Processing circuit 1040 also includes a hardware interface 1064 for supporting the execution of the computer code plant designator module 1052, target identifier module 1054, emitter aimer module 1056, deactivation confirmation module 1058, and report generator module 1062. Interface 1064 may include hardware configured to receive data as input to processing circuit 1045 (e.g. from an input device) and/or communicate data as output to another computing device (e.g., to a display). For example, processing circuit 1040 may receive plant data 1066 from one or more sensors (e.g., sensor 1030), databases, or remote computing devices. Interface 1064 may include circuitry to communicate data via any number of types of networks or other data communication channels. For example, interface 1064 may include circuitry to receive and transmit data via a wireless network or via a wired network connection. In another example, interface 1064 may include circuitry configured to receive or transmit data via a communications bus with other electronic devices.

Memory 1050 may include plant data 1066. In general, plant data 166 may include any data relating to the characteristics of one or more plants (e.g., plant type or species, the preferred method of deactivating the plant species, identifying characteristics of the plant species including spectroscopic data, the responsiveness of the plant species to non-visible light, genetic markers found in the plant species, etc.). In some embodiments, plant data 1066 may include sensor data generated by one or more sensors 1030 associated with system 1025 (e.g. size, amount, shape, color, chemical makeup, location, results of analysis on a sample, etc. of the detected plant material). Sensor data may include, but is not limited to, data regarding the type of plant material detected by a sensor, data regarding the location of the detected plant material, data regarding the motion of the detected plant material (e.g., speed, velocity, direction of travel, etc.), data regarding whether the detected plant material is deactivated (e.g., alive or dead), data regarding environmental conditions detected by a sensor (e.g., wind speed, wind direction, weather type including rain, snow, fog, etc., water direction, water speed, etc.), and data regarding the boundary between the growing region and the exclusion region. Plant data 1066 may also include user-provided data. User-provided data may include, but is not limited to, data regarding types of plant material, data regarding the plant material or materials to be deactivated, data regarding the boundary between the growing region and the exclusion region, data regarding the types of plant materials found within the growing region and within the exclusion region, and data regarding the components of the system to be controlled by the processing circuit.

Memory 1050 may include plant designator module 1052. Plant designator module 152 may be configured to designate the plant material or materials to be deactivated by system 1025. In some embodiments, plant designator module 1052 may receive a user input specifying the plant material.

Memory 1050 may include target identifier module 1054. Target identifier module 1054 may be configured to determine the location of detected plant material relative to the emitter. In some embodiments, target identifier module 1054 specifies detected plant material as targeted for deactivation by the emitter when the detected plant material is in the exclusion region and has been determined to be a specific type plant material (e.g., a sample of the plant material has been gathered and analyzed to determine the specific type of plant material). In some embodiments, target identifier module 1054 plots the boundary separating the growing region from the exclusion region (e.g., in response to a user input, in response to a sensor input, for example, from a GPS sensor, in response to the location of the emitter, in response to the location of the sensors, etc.)

Memory 1050 may include emitter aimer module 1056. Emitter aimer module 1056 may be configured to aim the emitter at the targeted plant material and activate or fire the emitter at the targeted plant material. In some embodiments, emitter aimer module 1056 causes a movable emitter to move to aim at the targeted plant material. In some embodiments, emitter aimer module 1056 causes a vehicle to which the emitter is attached to move in order to aim at the targeted plant material. In some embodiments, emitter aimer module 1056 selects one or more emitters from a group of stationary emitters for activation. In some embodiments, a separate emitter activation module is configured to activate or fire the emitter at the targeted plant material, not the emitter aimer module 1056.

Memory 1050 may include deactivation confirmation module 1058. Deactivation confirmation module 1058 may be configured to determine when the targeted plant material has been successfully or unsuccessfully deactivated by the emitter. In some embodiments, deactivation confirmation module 1058 receives data from the sensors and compares that data to data regarding targeted plant material to determine if the targeted plant material has been successfully or unsuccessfully deactivated (e.g., if growing plant material no longer found at the location at which it was previously detected). In some embodiments, deactivation confirmation module 1058 implements a feedback loop with target identifier module 1054 and emitter aimer module 1056 so that the unsuccessfully deactivated plant material is retargeted until it has been successfully deactivated. For example, deactivation confirmation module 1058 may operate the sensors to confirm that growing plant material previously targeted for deactivation and/or collection is no longer present. This confirmation can be made periodically at an appropriate time (e.g., 1 hour, 6 hours, 1 day, 1 week, etc.) following the deactivation and/or collection operation. The appropriate time may vary depending on the types of sensors used to detect the plant material and on the type of equipment used to carry out the deactivation and/or collection operation.

Memory 1050 may include report generator module 1062. Report generator module 1062 may be configured to track and store data related to the sensors and/or the emitters. In some embodiments, report generator module 1062 stores data related to the number of plant material detected by the sensor, the number of successful deactivations by the emitter, the number of unsuccessful deactivations by the emitter and generates a report of the effectiveness of the emitter or system that can be displayed to a user or otherwise output for other uses. In some embodiments, report generator module 1062 stores data related to the number, amount, quantity, etc. of plant material detected by the sensor, the direction of plant material exiting the growing region 115, the portion of the boundary 105 where plant material is exiting the growing region 115, and generates a report containing this data or other information (e.g., information generated using this data as an input) that can be displayed to a user or otherwise output for other uses.

In some embodiments, system 1025 includes a display, an input device, a communication device, and/or a mapping device similar to those discussed above with respect to system 125.

Sensor 1030 detects growing plant material (i.e., at a distance from sensor 1030 itself). In some embodiments, sensor 1030 comprises an imaging sensor. The imaging sensor is capable of visually detecting and determining the location of growing plant material. The imaging sensor may be used in combination with a light source (e.g., to illuminate plant material that is responsive to UV-light or other light spectrums).

Emitter device 1035 may target growing plant material 170 detected by sensor 130 in exclusion region 120 (e.g., growing plant material 170 on the ground). Emitter device 1035 emits an emission as described above to deactivate the growing plant material. In some embodiments, system 1025 includes multiple emitter devices 1035, each employing a different one of the methods for deactivating plant material described above. In this way, a combination of methods for deactivation can be used when attempting to deactivate plant material. In other embodiments, system 1025 includes multiple emitter devices 1035, each employing the same method for deactivating plant material. In this way, the multiple emitter devices 1035 provide redundancy in case of failure or malfunction of one of the emitter devices 1035. In some embodiments, a vehicle as described above is used to collect the deactivated plant material.

Referring to FIG. 14, system 1125 is another exemplary embodiment of a system for deactivating plant material. System 1125 is similar to systems 1025 and may include, in various embodiments, components similar to those described above with respect to system 1025. System 1125 includes imaging sensor 1130, emitter device 1135, processing circuit 1140, vehicle 1143, and plant sensor 1146. In some embodiments, emitter device 1135 is omitted from system 1125 and vehicle 1143 deactivates the growing plant material with an emitter device and/or deactivation implement. In some embodiments, system 1125 includes multiple imaging sensors 1130, emitter devices 1135, ground vehicles 1143, and/or plant sensors 1146.

Sensor 1130 comprises an imaging sensor as described above for visually detecting and determining the location of growing plant material. Sensor 1130 may detect multiple instances of growing plant material in exclusion region 120. The location of detected growing plant material may be stored as plant data by processing circuit 1140. Sensor 1130 may be a component of the same structure as emitter device 1135, a component of vehicle 1143, or part of a separate freestanding support or housing. System 1125 may include multiple imaging sensors.

Processing circuit 1140 may be found in the same unit or housing as sensor 1130, emitter device 1135, vehicle 1143, sensor 1146, or as a separate component (e.g., as a component of a control station). Sensor 1130, emitter device 1135, vehicle 1143, and sensor 1146 may be in wireless communication with processing circuit 1140.

Vehicle 1143 includes sampling implement 1148 for collecting a sample of growing plant material 170 for analysis by plant sensor 1146. Sampling implement 1148 is configured to physically collect a sample from growing plant material 170. For example, sampling implement 1148 may be one or more blades, needles, manipulator arms, vacuums, swabs, wipes, or other device suitable to collecting plant material sample. Plant sensor 1146 may be onboard vehicle 1143 or at another location (e.g., a control station). Vehicle 1143 may be a ground vehicle or an air vehicle.

In some embodiments, sensor 1146 comprises a spectroscopic sensor. The spectroscopic sensor (e.g., a spectrometer, a spectrophotometer, a spectrograph, a spectral analyzer, etc.) is capable of detecting and identifying a signature indicative of plant material via spectroscopy (e.g. optical spectroscopy, ultraviolet spectroscopy, infrared spectroscopy, X-ray spectroscopy, active spectroscopy, laser-induced breakdown spectroscopy, etc.). In some embodiments, sensor 1146 comprises a biosensor. The biosensor is capable of detecting and identifying a component or analyte of the plant material indicative of the plant material. In some embodiments, the component may be responsive to nonvisible light (e.g. ultraviolet or infrared light). In some embodiments, the component is a genetic marker. In some embodiments, the genetic marker is naturally occurring. In other embodiments, the plant material has been genetically modified to express, contain, or otherwise incorporate the genetic marker. In some embodiments, the biosensor may identify a component or analyte of the plant material indicative of the plant material (e.g., by direct analysis of the plant material following physical collect of a sample of the plant material by a manipulator arm, a shovel, a spade, a vacuum, or other appropriate sample collection device). Genetic markers may in some cases be selected to produce readily detectable characteristics of the plant material (e.g., fluorescence of green fluorescent protein, or production of a distinctive surface coloration or other physical feature of plants or seeds). In other cases, genetic markers may be natural or artificial gene patterns (e.g., mutations for resistance to a plant disease, which produce no externally detectable features but which can be detected by appropriate biological or biochemical analysis (e.g., polymerase chain reaction)). An artificial gene pattern may be selected so that the gene pattern expresses a phenotype (e.g., fluorescing in response to exposure to light) detectable by a sensor. For example, green fluorescent protein (GFP) is a protein that exhibits bright green fluorescence when exposed to light in the blue to ultraviolet range. Other detectable phenotypes includes distinctive shapes or sizes of the plant material (e.g., height to width ratio of the plant or a component of the plant), the color of the plant material and the presence or absence of one or more specific chemicals. Different types of biosensors are able to perform remote analysis and local analysis of a sample of plant material. Both these types of analysis may be spectroscopic. Different types of biosensors may detect a gene or gene pattern itself (e.g., with polymerase chain reaction, or other appropriate technique) or detect the expression of the gene or gene pattern. As discussed above, the expression may be physical, chemical, or biological. For example, the expression may be a protein that is relatively easy to identify.

Data regarding samples, the location of the plant material from which each sample was taken, results of analysis performed by sensor 1146, etc. is stored in the processing circuit 1140 (e.g., as plant data).

Sensor 1146 may be capable of detecting more than one type of plant material; however, system 1125 deactivates specific types of plant material 170 (e.g., a specific species, strain, etc. of plant). For example, sensor 1146 may be capable of detecting several types of plants, but only a specific genetically-modified plant is specified as the growing plant material for system 1125 to deactivate. The specific plant material designated to be deactivated may be specified manually by a user or automatically by system 1125. In some embodiments, the plant material is selected from a list of possible plant materials to be designated. In some embodiments, the user uses an input device to specify the plant material. In some embodiments, the plant material has been genetically-modified to be particularly susceptible to one or more specific methods of deactivation. For example, the plant material may be genetically modified to be particularly susceptible to a specific type of chemical and therefore easier to deactivate with a system using that chemical. As another example, the plant material may be genetically modified to be particularly susceptible to heat and therefore easier to deactivate with a laser or other heat delivery method of deactivation.

When sensor 1146 determines that a sample of plant material is the specific plant material designated to be deactivated, system 1125 automatically deactivates the plant material from which the sample was taken. Emitter device 1135 may be used to deactivate the plant material. Vehicle 1143 may include an emitter device and/or a deactivation implement so that vehicle 1143 may be used to deactivate and/or collect the plant material. In some embodiments, vehicle 1143 includes an identifier device (e.g., similar to identifier device 957 described above) that identifies or marks the plant material by providing an identification. Identifier device may mark all plant material from which a sample is taken or may mark only the plant material for which its sample is determined to be the designated plant material. This identification may take the form of a physical marking such as a paint or dye emitted by a physical marking emitter that can be detected by sensor 1130 or a separate identification sensor located on vehicle 1143 or elsewhere (e.g., visible to an imaging sensor or detectable by another appropriate type of sensor to identify the physically marked plant material), or the storing of location information (e.g., on a coordinate system describing the exclusion region 120, as a GPS coordinate, etc.) in memory (e.g., as plant data) that can be identified by retrieving the location information from memory. The physical marking may respond to electromagnetic radiation (visible light, nonvisible light like ultraviolet or infrared, etc.), with a response for example, through fluorescence or phosphorescence. This response may be detected by sensor 1130 or a separate identification sensor (e.g., an imaging sensor, a light sensor, or other appropriate type of sensor to identify the response).

Vehicle 1143 may be controlled to perform various types of patrols from plant material in the exclusion region 120. For example, vehicle 1143 may be dispatched on a sampling patrol in which it gathers samples from each instance of growing plant material identified by sensor 1130. Sensor 1146 analyzes these samples. Vehicle 1143 may then be dispatched on a deactivation patrol in which it deactivates the instances of plant material that are determined to need deactivation based on analysis by sensor 1146. Alternatively, sampling and deactivating could be combined in a single patrol. Certain types of vehicles, such as small vertical-takeoff-and-landing UAVs, may be particularly well suited to performing physical sampling missions quickly and at low cost. Such a UAV may also be able to carry plant analysis sensors and/or deactivation equipment, or may be supplemented with one or more fixed base stations having sample analysis sensors and/or larger UAVs carrying deactivation equipment. Multiple vehicles may be used to perform complimentary tasks. For example, a first vehicle could conduct regular patrols to identify plant material to be deactivated and a second vehicle could be dispatched periodically to deactivate plant material targeted for deactivation based on the first vehicle's identification. One or more vehicles may also be used with a base station to perform complimentary tasks. For example, a first vehicle could conduct regular patrols to gather plant material samples and return to the base station where the gathered samples are analyzed (e.g., a spectroscopic analysis). The first vehicle, or a second vehicle, could then be dispatched to deactivate targeted plant material based on the analysis performed at the base station.

Figure 15:
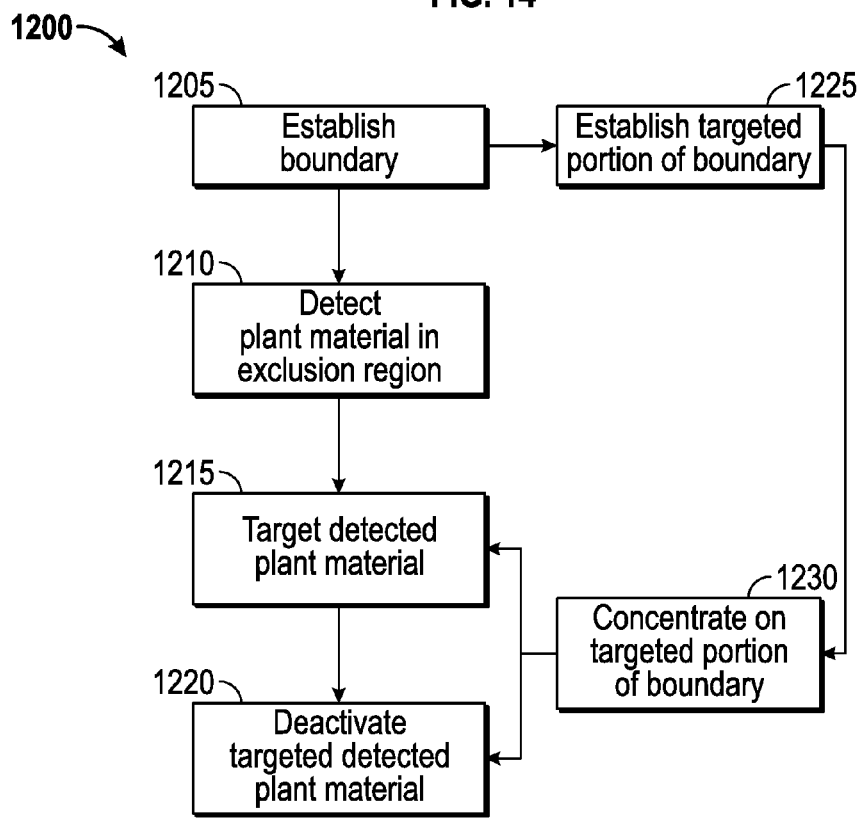
FIG. 15 is a flow chart of a method of deactivating plant material according to an exemplary embodiment.

Referring to FIG. 15, a method of deactivating plant material 1200 is illustrated according to an exemplary embodiment. In some embodiments, method 1200 is implemented by system 1025. A boundary (e.g., boundary 105) is established separating a growing region (e.g., growing region 115) from an exclusion region (e.g., exclusion region 120) (step 1205). Growing plant material (e.g. plant material 170) is detected (e.g., by sensor 1030) in the exclusion region (step 1210). The detected plant material is targeted (e.g., by emitter device 1035) (step 1215). An emission as described above or other substance to deactivate plant material, is emitted at the targeted detected plant material to deactivate the targeted detected plant material (step 1220). Alternatively, a deactivation implement is used in place of or in addition to the emission to deactivate the targeted detected plant material.

In some embodiments, method 1200 also includes establishing a targeted portion (e.g. side 105B) of the boundary (e.g., boundary 105) (step 1225). In some embodiments, the targeted portion of the boundary is identified in response to known circumstances likely to result in plant material exiting the growing region to the exclusion region at the targeted portion of the boundary. For example, wind direction may dictate the direction and location from which airborne plant material can be expected to exit the growing region. As another example, moving sources of water (e.g., stream, river, etc.) are known to flow in a specific direction, which will dictate the direction and location from which waterborne plant material can be expected to exit the growing region. As another example, the reproductive cycle of the plants within different portions of the growing region is known and the portions of the boundary close to the portions of the growing region expected to produce reproductive components (e.g., seeds, pollen, spores, etc.) or runners would be the targeted portion of the boundary. Targeting (steps 1215) and emitting (step 1220) is concentrated on the targeted portion of the boundary (e.g., by increasing vehicle patrol time along the targeted portion of the boundary, by increasing number of sensors and/or emitter devices along the targeted portion of the boundary, etc.) (step 1230). In this way, more plant material deactivating resources are brought to bear along the targeted portion of the boundary.

Figure 16:
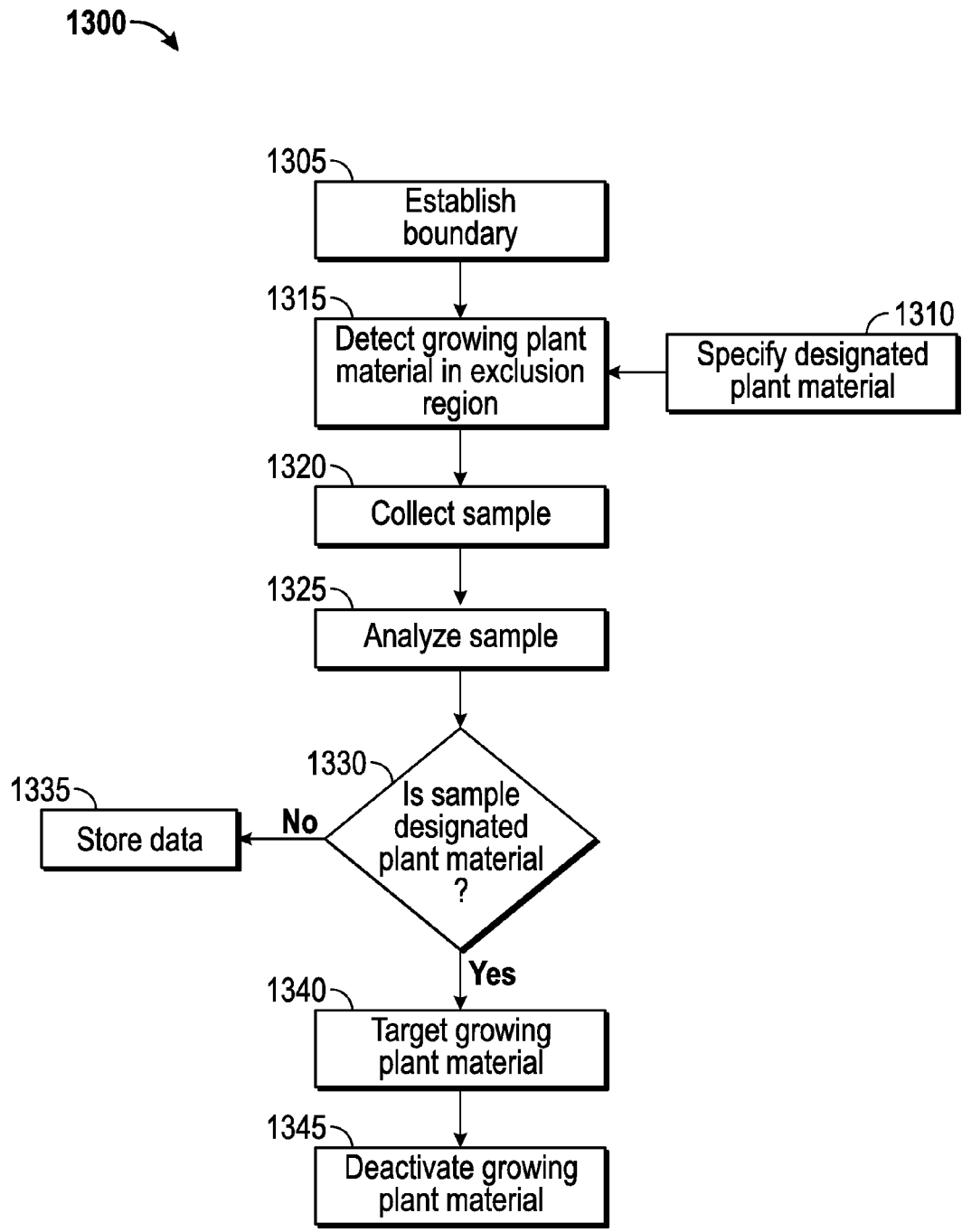
FIG. 16 is a flow chart of a method of deactivating plant material according to an exemplary embodiment.

Referring to FIG. 16, a method of deactivating plant material 1300 is illustrated according to an exemplary embodiment. In some embodiments, method 1300 is implemented by system 1125. A boundary (e.g., boundary 105) is established separating a growing region (e.g., growing region 115) from an exclusion region (e.g., exclusion region 120) (step 1305). A specific type or types of plant material are designated as those to be deactivated by the system (e.g., by a user input) (step 1310). Growing plant material (e.g. plant material 170) is detected (e.g., by sensor 1130) in the exclusion region (step 1315). A sample is collected from the detected growing plant material (e.g., by sampling implement 1148 of vehicle 1143) (step 1320). The sample is analyzed (e.g., by plant sensor 1146) (step 1325) to determine if the growing plant material it was sampled from is the designated plant material (step 1330). If the sample is not the designated plant material, this information may be stored as data (e.g., as plant data by processing circuit 1140) (step 1335) or no further action may be taken. The stored data may be used so that the growing plant material determined to not be the designated plant material is not subsequently sampled by the system. If the sample is the designated plant material, the growing plant material from which the sample was taken is targeted for deactivation (step 1340). The targeted designated plant material is then deactivated (e.g., by emitter device or deactivation implement) (step 1345) In some embodiments, the deactivated plant material is then collected (e.g., by vehicle 1143).

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show or the description may provide a specific order of method steps, the order of the steps may differ from what is depicted. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for deactivating plant material outside of a growing region, comprising:
    an emitter device configured to deactivate a plant material;
    a sensor configured to remotely detect a presence of the plant material outside of a boundary defining the growing region; and
    a controller configured to aim and activate the emitter device to deactivate the plant material in response to the plant material being detected by the sensor.

2. The system of claim 1, wherein the plant material comprises a plant.

3. The system of claim 1, wherein the plant material comprises a reproductive component of a plant.

4. The system of claim 1, wherein the plant material comprises transgenic plant material.

5. The system of claim 1, wherein the controller is further configured to aim and activate the emitter device at stationary plant material.

6. The system of claim 1, wherein the controller is further configured to aim and activate the emitter device at moving plant material.

7. The system of claim 6, wherein the moving plant material is airborne.

8. The system of claim 6, wherein the moving plant material is waterborne.

9. The system of claim 1, wherein the sensor comprises an imaging sensor.

10. The system of claim 1, wherein the sensor comprises a radar device.

11. The system of claim 1, wherein the sensor comprises a LIDAR device.

12. The system of claim 1, wherein the sensor is configured to detect a component of the plant material.

13. The system of claim 12, wherein the component is responsive to nonvisible light.

14. The system of claim 12, wherein the component is responsive to ultraviolet light.

15. The system of claim 1, wherein the sensor is configured to detect an expression of a genetic marker of the plant material.

16. The system of claim 1, wherein the emitter device comprises a movable beamed energy emitter.

17. The system of claim 1, wherein the emitter device comprises a movable chemical emitter.

18. The system of claim 1, wherein the emitter device comprises a movable high temperature emitter.

19. The system of claim 1, wherein the emitter device comprises a plurality of fixed beamed energy emitters, each fixed beamed energy emitter producing a deactivation zone, and wherein the controller is further configured to identity the deactivation zone that includes the plant material detected by the sensor and activate the corresponding fixed beam energy emitter.

20. The system of claim 1, wherein the emitter device comprises a plurality of fixed chemical emitters, each chemical emitter producing a deactivation zone, and wherein the controller is further configured to identity the deactivation zone that includes the plant material detected by the sensor and activate the corresponding chemical emitter.

21. The system of claim 1, wherein the emitter device comprises a plurality of fixed high temperature emitters, each high temperature emitter producing a deactivation zone, and wherein the controller is further configured to identity the deactivation zone that includes the plant material detected by the sensor and activate the corresponding high temperature emitter.

22. The system of claim 1, further comprising:
a vehicle to which the emitter device is mounted.

23. The system of claim 1, further comprising:
a mapping device, wherein the controller is further configured to receive data from the mapping device and plot the growing region.

24. A method of deactivating plant material, comprising:
establishing a boundary separating a growing region from an exclusion region;
remotely detecting a plant material in the exclusion region;
targeting the detected plant material in the exclusion region; and
emitting an emission at the targeted detected plant material to deactivate the targeted detected plant material.

25. A system for deactivating plant material outside of a growing region, comprising:
an emitter device configured to deactivate a plant material;
a plurality of sensors configured to remotely detect a presence of the plant material outside of a boundary defining the growing region; and
a controller configured to aim and activate the emitter device to deactivate the plant material in response to the plant material being detected outside of the growing region by one or more of the sensors.

26. The system of claim 25, wherein the plant material comprises a plant.

27. The system of claim 25, wherein the plant material comprises a reproductive component of a plant.

28. The system of claim 25, wherein the plant material comprises transgenic plant material.

29. The system of claim 25, wherein the controller is further configured to aim and activate the emitter device at stationary plant material.

30. The system of claim 25, wherein the controller is further configured to aim and activate the emitter device at moving plant material.

31. The system of claim 25, wherein the emitter device comprises a movable beamed energy emitter.

32. The system of claim 25, wherein the emitter device comprises a movable chemical emitter.

33. The system of claim 25, wherein the emitter device comprises a movable high temperature emitter.

34. The system of claim 25, wherein the emitter device comprises a plurality of fixed beamed energy emitters, each fixed beamed energy emitter producing a deactivation zone, and wherein the controller is further configured to identity the deactivation zone that includes the plant material detected by at least one of the sensors and activate the corresponding fixed beam energy emitter.

35. The system of claim 25, wherein the emitter device comprises a plurality of fixed chemical emitters, each chemical emitter producing a deactivation zone, and wherein the controller is further configured to identity the deactivation zone that includes the plant material detected by at least one of the sensors and activate the corresponding chemical emitter.

* * * * *